(12) United States Patent
Hampel

(10) Patent No.: US 8,130,899 B2
(45) Date of Patent: Mar. 6, 2012

(54) ARRANGEMENT FOR ELECTRON BEAM TOMOGRAPHY

(75) Inventor: Uwe Hampel, Dresden (DE)

(73) Assignee: Helmholtz-Zentrum Dresden-Rossendorf E.V., Dresden (DE)

( * ) Notice: Subject to any disclaimer, the term of this patent is extended or adjusted under 35 U.S.C. 154(b) by 148 days.

(21) Appl. No.: 12/752,342

(22) Filed: Apr. 1, 2010

(65) Prior Publication Data

US 2010/0254507 A1 Oct. 7, 2010

(30) Foreign Application Priority Data

Apr. 1, 2009 (DE) .................... 10 2009 002 114

(51) Int. Cl.
*H05G 1/02* (2006.01)
(52) U.S. Cl. .......................... 378/10; 378/137
(58) Field of Classification Search ............ 378/4, 10, 378/12, 19, 145, 146, 137, 138, 143, 124
See application file for complete search history.

(56) References Cited

U.S. PATENT DOCUMENTS

| | | | |
|---|---|---|---|
| 4,260,885 A * | 4/1981 | Albert | 378/45 |
| 4,352,021 A | 9/1982 | Boyd et al. | |
| 6,687,332 B2 * | 2/2004 | Smyth | 378/113 |
| 6,983,035 B2 * | 1/2006 | Price et al. | 378/124 |
| 7,023,950 B1 | 4/2006 | Annis | |
| 7,580,500 B2 | 8/2009 | Forster et al. | |

FOREIGN PATENT DOCUMENTS

DE 102007019176 A1 1/2008

* cited by examiner

*Primary Examiner* — Hoon Song
(74) *Attorney, Agent, or Firm* — Laurence A. Greenberg; Werner H. Stemer; Ralph E. Locher

(57) ABSTRACT

An assembly for electron beam tomography affords continuous and simultaneous recording of two-dimensional slice images of an object in different irradiation planes with a high temporal and spatial resolution. Targets are penetrated by openings of a given width and with a regular arrangement in the circumferential direction. The openings in the targets are respectively situated on a path formed by the cross section of the shell of the electron beam cone with the respective target. The successive targets in the beam direction respectively are arranged with a small angular offset with respect to the optical axis to the respective target situated in front, and so an electron beam circulating along the shell of the electron beam cone successively irradiates the material webs between the openings of all targets with at least part of its cross section and an X-ray detector arc is arranged for each target in coplanar radial fashion in front of or behind the respective target.

3 Claims, 1 Drawing Sheet

… (US 8,130,899 B2)

ARRANGEMENT FOR ELECTRON BEAM TOMOGRAPHY

CROSS-REFERENCE TO RELATED APPLICATION

This application claims the priority, under 35 U.S.C. §119, of German patent application DE 10 2009 002 114.0, filed Apr. 1, 2009; the prior application is herewith incorporated by reference in its entirety.

BACKGROUND OF THE INVENTION

Field of the Invention

The invention relates to an arrangement for X-ray computed tomography with a scanned electron beam.

These days, electron beam tomography is used for flow examinations of multiphase flows and in medical diagnostics, particularly for imaging the beating heart (Fischer et al., Meas. Sci. Technol. 19, pp. 094002, 2008). In the process, an electromagnetic deflection system guides an electron beam, guided in a vacuum chamber, over a partly annular metal target and this generates an X-ray focal point that can be moved quickly. An annular or partly annular X-ray detector arc arranged with a slight axial offset with respect to the target registers the X-ray radiation penetrating the examination object. This measurement data can be used to calculate the material distribution in the irradiated slice plane by applying tomographic image reconstruction methods.

The particular advantage of electron beam tomography lies in the high achieveable frame rate as a result of being able to deflect the inertia-free electron beam quickly with the aid of alternating magnetic fields. In principle, this arrangement initially only allows the generation of slice images in one irradiation plane. In principle, records of different layers of the examination object are afforded by axial movement of the examination object or scanner. However, such a mechanical movement requires too much time to be able simultaneously to image fast changes in the examination object in different irradiation planes. Quasi-simultaneous recording of slice images in different irradiation planes is afforded by, for example, the electron-beam scanner disclosed in U.S. Pat. No. 4,352,021. There, the electron beam successively can be guided over various target segments situated behind one another in the axial direction. However, because only a single X-ray detector arc is used in that assembly, the slice plane separation must be kept small in order to avoid axial image blurring resulting from the non-coplanar arrangement of focal-point path and X-ray detector arc. A further disadvantage of this arrangement consists of the images in different axial slice planes being recorded successively and not simultaneously. As a result of this, no information relating to the material distribution in the other irradiation planes can be recorded during the scan movement of the electron beam over the target region assigned to a particular irradiation plane. This is a decisive disadvantage, particularly in applications of electron beam tomography examining fast processes, such as multiphase flows, because information is lost in the sequential scanning of planes.

U.S. Pat. No. 7,580,500 B2 and its corresponding German published patent application DE 10 2007 019 176 A1 describe a computed tomography scanner with discrete focal areas on the target that are arranged in a saw-tooth fashion. The disadvantage of this arrangement is that the focal areas have to be produced laboriously and the arrangement appears to be very complicated because the individual areas have to be adjusted.

U.S. Pat. No. 7,023,950 B1 describes an arrangement for irradiating materials, products or commodities to be examined by X-ray beams, wherein the target is subdivided into sections (e.g. by applying highly-emissive material) and so the location of the X-ray beam can be determined.

SUMMARY OF THE INVENTION

It is accordingly an object of the invention to provide an electron beam tomography assembly which overcome the above-mentioned disadvantages of the heretofore-known devices and methods of this general type and which affords a continuous multi-plane scan with virtually simultaneous recording of slice images of a number of irradiation planes in an examination object with a high temporal and spatial resolution.

With the foregoing and other objects in view there is provided, in accordance with the invention, an assembly for electron beam tomography, comprising:

a device for generating, focusing, and deflecting an electron beam within a vacuum chamber;

annular or partly annular targets arranged successively along a beam direction within the vacuum chamber for decelerating the electron beam;

a plurality of X-ray detector arcs formed of individual detectors placed next to one another, the X-ray detector arcs being disposed in a coplanar relation and with a slight axial offset to the targets;

a recording aperture for an examination object; and detector diaphragms configured to suppress scattered radiation;

each target having openings of a given width formed therein and material webs therebetween, regularly arranged in a circumferential direction;

the openings in the targets being respectively situated on a path formed by a cross section of a shell of an electron beam cone with the respective the target, with a tip of the electron beam cone being defined in space by a deflection point of the electron beam and a shell thereof through the paths of the electron beam;

the targets, following a forward-most target in the beam direction, respectively being disposed with a small angular offset with respect to an optical axis to the respective the target situated in front, and with an electron beam circulating along the shell of the electron beam cone successively irradiating the material webs between the openings of all targets with at least part of cross section thereof; and an X-ray detector arc for each the target disposed in coplanar fashion and in a radial direction in front of or behind the respective the target.

In other words, the objects of the invention are achieved by way of an arrangement for electron beam tomography with a multiplicity of specially shaped, successively arranged targets and a multiplicity of fixed X-ray detector arcs.

A particular advantage of the novel assembly for electron beam tomography consists of the fact that it affords concurrent recording of two-dimensional slice images of an object in various irradiation planes at a high frame rate. Hence, the novel configuration is suited to a number of diagnostic problems in which dynamic processes are intended to be examined. The measurement of multiphase flows constitutes an example thereof, where the velocities of structures in the flow can be determined by fast and concurrent imaging in two or more irradiation planes.

In accordance with an added feature of the invention, a diameter of the electron beam is less than a width of the material web such that, at any one time, a focal point with a full bremsstrahlung power is generated in each case on only one of the targets.

In accordance with a concomitant and alternative feature of the invention, the electron beam diameter is greater than a width of the material web such that, at any one time, a focal point with part of a bremsstrahlung power is generated on a plurality of targets.

Other features which are considered as characteristic for the invention are set forth in the appended claims.

Although the invention is illustrated and described herein as embodied in an arrangement for electron beam tomography, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
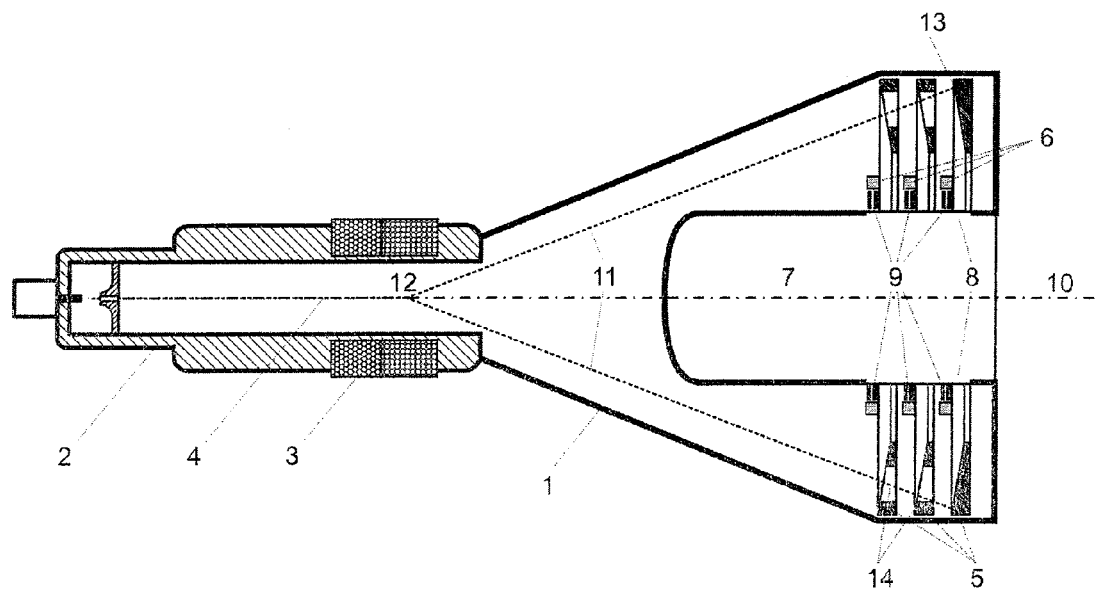
FIG. 1 is a diagrammatic longitudinal section taken through the assembly according to the invention.

Referring now to the figures of the drawing in detail and first, particularly, to FIG. 1 thereof, there is shown a device according to the invention which comprises the following components: a vacuum chamber 1 surrounding the electron beam system, an electron gun 2, an electron-optical system 3 for focusing the electron beam 4 emanating from the electron gun 2, and for deflecting the beam in two dimensions. The assembly further includes a plurality of specially formed targets 5 for generating the X-ray beam, and a plurality of X-ray detector arcs 6, a recording aperture 7 for the examination object, in which, in the interior, the wall of the vacuum chamber 1 has been thinned to form an X-ray beam outlet window 8, and detector diaphragms 9.

Further optional components, not listed explicitly here but known to those of skill in the pertinent art, are sensors for measuring and monitoring important operating parameters (target temperature, quality of the vacuum, electron beam parameters), electronics components for registering measurement values, generating high and auxiliary voltages and guiding the beam, components for hardening the beam, shielding components, a couch or supports for the examination object, a cooling apparatus for the target, etc.

In the undeflected state, the electron beam 4 leaves the electron gun 2 in a straight line through the anode bore. The imaginary straight line from the cathode (electron source) to the anode bore is hereafter referred to as the optical axis 10. The electron-optical system 3 deflects the electron beam 4 emanating from the electron gun 2 from the direction of the optical axis 10 by an angle $\alpha$ and causes the electron beam to rotate about the optical axis 10. As a result of this, the electron beam 4 propagates on the imagined shell of an electron beam cone 11, the tip of which being the deflection point 12 of the electron beam 4 in the deflection coil system of the electron-optical system 3. In general, the time-dependent deflection is given by the mathematical function $\alpha(\omega t)$ where $\omega$ is the angular frequency of the rotation. In the case of annular or partly annular targets 5 perpendicular to the optical axis 10, the electron beam 4 is rotated about the optical axis 10 in a circle and so the focal point 13 created on a target 5 moves in a circular orbit.

The partly or completely annular targets 5 are arranged successively in the electron beam direction in the head-side part of the vacuum chamber 1. The targets 5 are metal rings which have a surface slightly angled to the perpendicular of the optical axis 10 and are perforated by a multiplicity of openings 14 that are distributed regularly on the circumference and are led away from the optical axis 10 in a radial fashion.

The width of the openings 14 in the circumferential direction is referred to by B, the spacing between the openings 14 in the circumferential direction by W and the width of the material web 15 between the openings 14 in the circumferential direction is S=W−B.

The openings 14 can be dispensed with in the last target 5 in the electron beam direction.

Figure 2:
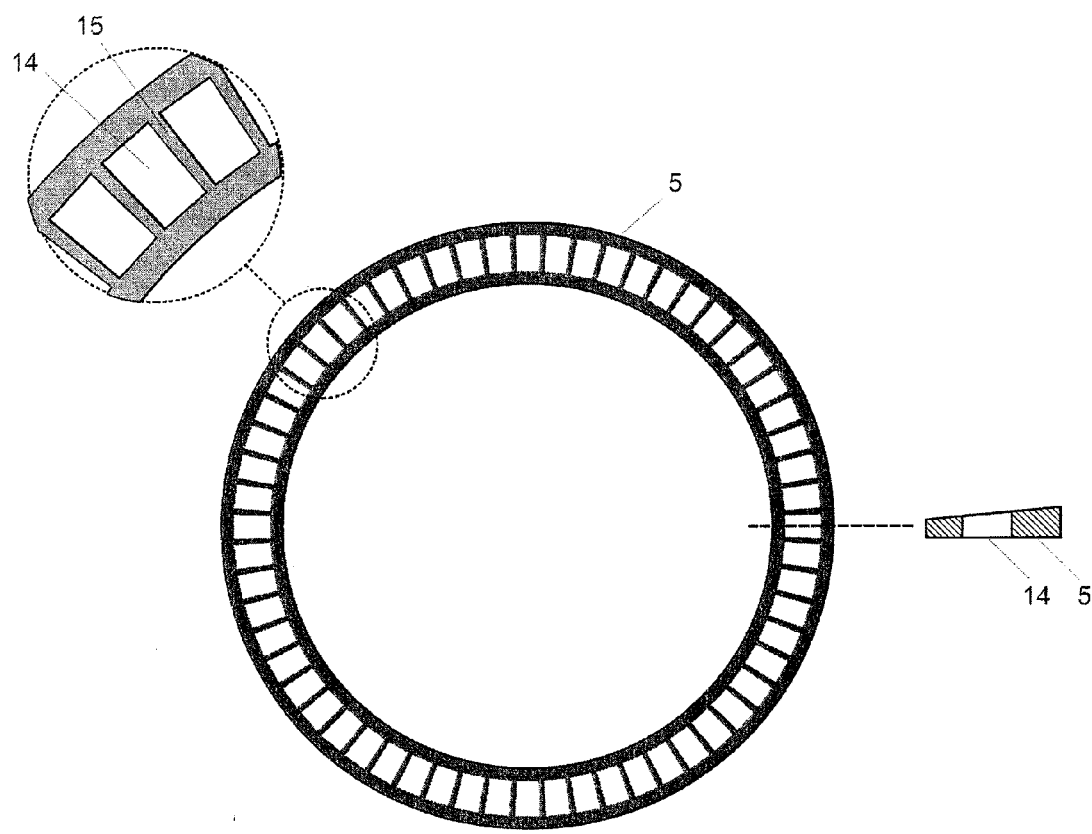
FIG. 2 shows a view of the target arrangement according to the invention.

The width of the openings 14 B should be selected such that W/S=W/(W−B)=N holds true, where N refers to the number of targets 5 (see FIG. 2). With respect to the optical axis 10, the N successive targets 5 are arranged by an angular offset of $\Delta\alpha/N$ relative to a fixed reference angle, which is identical for all targets 5, with the arc separation $\Delta\alpha$ between two adjacent openings 14.

If the electron beam 4 sweeps over the material web 15 between the openings 14 of the front-most target 5 in the electron beam direction, X-ray radiation is generated, in the metal layer at the surface, within a focal point 13 determined by the focusing as a result of electron deceleration. If the electron beam 4 sweeps over one of the openings 14 of the front-most target 5 in the electron beam direction, it passes therethrough and impinges on the second target 5 lying therebelow. As a result of the slight angular offset of this target 5 with respect to the first target 5, the electron beam 4 once again briefly sweeps over a material web 15 between the openings 14 of the second target 5, as a result of which X-ray radiation is generated in the second irradiation plane. When the electron beam 4 continues to move, it passes through the openings 14 of the first and second targets 5 and sweeps over the material web 15 between the openings 14 in the target 5 lying third in the electron beam direction. This continues according to the number of targets 5 present, until the electron beam 4 once again sweeps over a material web 15 of the upper-most target 5.

Variants of the target impingement by the electron beam 4 emerge from the type of beam focusing. On the one hand, it is possible to focus the electron beam 4 as sharply as possible such that the diameter of the focal point 13 is less than the width of the material web 15 S. This means that irradiation projections in the individual irradiation planes are recorded successively in time because bremsstrahlung (i.e., braking radiation, free-free radiation) is in each case only generated on one target 5. During the circular movement of the electron beam 4, it may be advantageous in such a variant to refocus said beam electromagnetically according to the distance to the impinged target 5 using the focusing coils of the electron-optical system 3.

A further variant consists of the focal point 13 having a very large design, for example of the order of the spacing between the openings 14 W. In this case, the electron beam 4 simultaneously produces focal points 13 on a plurality of targets 5 with part of the effective cross-section thereof. This allows concurrent registration of irradiation projections in a multiplicity of irradiation planes, albeit at the price of a correspondingly reduced X-ray radiation power per irradiation plane.

In order to register the X-ray radiation penetrating the examination object, an annular or partly annular X-ray detector arc 6 is arranged in a coplanar fashion with each target. Said arc consists of a multiplicity of individual detectors aligned next to one another to form an arc. The X-ray detector arc 6 is connected to special electronics (not illustrated in the image) that very quickly register and store the signals from the individual detectors of the X-ray detector arc 6.

Targets 5 and X-ray detector arcs 6 are arranged in planes with a slight axial offset to one another. If targets 5 or X-ray detector arcs 6 are only of a partly annular design, the arc length and arrangement in terms of angles of these components should be designed such that these ensure a complete angular scan of the Radon space of the irradiation plane, known to a person skilled in the art.

The following refinement variants are likewise assumed to be known to those of skill in the art:

- As a result of the slight angle of the target surface facing the electron beam 4 relative to the irradiation plane, the size of the projection of the focal point 13 in the direction of the optical axis 10 can be reduced.
- Arranging detector diaphragms 9 in front of the X-ray detector arcs 6 can prevent the ingress of scattered radiation or the ingress of radiation simultaneously generated on targets 5 outside of the observed irradiation plane.

The invention claimed is:

1. A configuration for electron beam tomography, comprising:
    a device for generating, focusing, and deflecting an electron beam within a vacuum chamber;
    annular or partly annular targets arranged successively along a beam direction within said vacuum chamber for decelerating the electron beam;
    a plurality of X-ray detector arcs formed of individual detectors placed next to one another, said X-ray detector arcs being disposed in a coplanar relation and with a slight axial offset to said targets;
    a recording aperture for an examination object; and
    detector diaphragms configured to suppress scattered radiation;
    each target having openings of a given width formed therein and material webs therebetween, regularly arranged in a circumferential direction;
    said openings in said targets being respectively situated on a path formed by a cross section of a shell of an electron beam cone with the respective said target, with a tip of the electron beam cone being defined in space by a deflection point of the electron beam and a shell thereof through the paths of the electron beam;
    said targets, following a forward-most target in the beam direction, respectively being disposed with a small angular offset with respect to an optical axis to the respective said target situated in front, and with an electron beam circulating along the shell of the electron beam cone successively irradiating said material webs between said openings of all targets with at least part of cross section thereof; and
    an X-ray detector arc for each said target disposed in coplanar fashion and in a radial direction in front of or behind the respective said target.

2. The configuration according to claim 1, wherein a diameter of the electron beam is less than a width of said material web such that, at any one time, a focal point with a full bremsstrahlung power is generated in each case on only one of said targets.

3. The configuration according to claim 1, wherein the electron beam diameter is greater than a width of said material web such that, at any one time, a focal point with part of a bremsstrahlung power is generated on a plurality of targets.

* * * * *